United States Patent [19]
Dunn et al.

[11] Patent Number: 5,324,520
[45] Date of Patent: Jun. 28, 1994

[54] INTRAGINGIVAL DELIVERY SYSTEMS FOR TREATMENT OF PERIODONTAL DISEASE

[75] Inventors: Richard L. Dunn; Arthur J. Tipton, both of Fort Collins; Ronald J. Harkrader, Louisville; Jack A. Rogers, Fort Collins, all of Colo.

[73] Assignee: Vipont Pharmaceutical, Inc., New York, N.Y.

[21] Appl. No.: 46,396

[22] Filed: Apr. 13, 1993

Related U.S. Application Data

[63] Continuation of Ser. No. 742,719, Aug. 5, 1991, abandoned, which is a continuation of Ser. No. 286,456, Dec. 19, 1988, abandoned.

[51] Int. Cl.$^5$ .................... A61K 9/14; A61K 9/16; A61K 9/48; A61K 37/22
[52] U.S. Cl. ............................ 424/435; 424/426; 424/434; 424/450; 424/451; 424/486; 424/487; 424/489; 424/490; 436/829; 514/953; 514/963; 264/4.1; 264/4.33; 264/4.6; 264/4.7
[58] Field of Search ............. 424/422, 426, 435, 434, 424/486, 487, 451, 489, 490; 264/4.1, 4.33, 4.6, 4.7; 514/772.3, 963, 450, 953; 436/829

[56] References Cited

U.S. PATENT DOCUMENTS

| | | | |
|---|---|---|---|
| 4,175,326 | 11/1979 | Goodson | 424/435 X |
| 4,249,531 | 2/1981 | Heller et al. | 424/435 X |
| 4,568,535 | 2/1986 | Loesche | 424/435 |
| 4,569,837 | 2/1986 | Suzuki et al. | 424/435 |
| 4,774,091 | 9/1988 | Yamahira | 424/426 |

FOREIGN PATENT DOCUMENTS

| | | |
|---|---|---|
| 0244118 | 11/1987 | European Pat. Off. |
| 0297535 | 1/1989 | European Pat. Off. |
| 0330180 | 8/1989 | European Pat. Off. |
| 0375127 | 6/1990 | European Pat. Off. |

OTHER PUBLICATIONS

PCT Application Publication, WO 9003768 (Southern Research Institute), Apr. 19, 1990.
Patent Abstracts of Japan, vol. 10, No. 31 (C-327), Feb. 6, 1986 & JP 60184027, (Raion K. K.), Sep. 19, 1985.

Primary Examiner—Paul R. Michl
Assistant Examiner—Carlos Azpuru
Attorney, Agent, or Firm—Merchant, Gould, Smith, Edell, Welter & Schmidt

[57] ABSTRACT

A polymeric controlled delivery system is provided for use in treating periodontal disease. The delivery system in a variety of forms is placed directly in the infected gingival tissue where the chemotherapeutic agent is slowly released into the tissue and into the infected periodontal pocket by means of the gingival crevicular fluid originating in the gingival tissue.

15 Claims, No Drawings

INTRAGINGIVAL DELIVERY SYSTEMS FOR TREATMENT OF PERIODONTAL DISEASE

This is a continuation of application Ser. No. 07/742,719, filed Aug. 5, 1991, now abandoned, which is a continuation of application Ser. No. 07/286,456, filed Dec. 19, 1988, now abandoned.

BACKGROUND OF THE INVENTION

Periodontal disease or gum disease as it is often called can be defined as an infection and inflammation of the gingiva or gums and loss of underlying alveolar bone support. There are varying levels of severity of the disease. The mildest cases are clinically termed gingivitis (inflamed and bleeding gums). More severe cases are clinically known as periodontitis and can involve loss of bone support. Gingivitis is reversible and can often be eliminated with a thorough dental prophylaxis followed by improved personal oral hygiene procedures. If gingivitis is not controlled, the disease often progresses into periodontitis.

Periodontitis is not only characterized by bacterial infection and inflammation, it is also accompanied by the formation of periodontal pockets (spaces between the teeth and gums) and bone deterioration which can lead to tooth loss. Periodontitis is recurring, progressive, and episodic. There is no cure at this time. Effective treatment is to apply professional intervention to halt disease progression.

Professional intervention may involve surgical or nonsurgical procedures. Nonsurgical treatment consists of periodic professional scaling, root planing, and soft tissue curettage, in combination with conscientious home care by brushing and flossing on the part of the patient. Surgical treatment involves gingivectomy and flap surgery to recontour the soft and hard tissue around the diseased areas.

In recent years, it has become increasingly recognized that control of periodontitis may be possible with the use of antimicrobial agents delivered to the infected site. Systemic antibiotics taken orally or intramuscularly have been successfully used, but due to the concern about allergic responses, the development of resistance, and the treatment of the whole person rather than the specific infection site, their use is recommended only in the severest of periodontal cases.

Treatment by mouth rinse and other topically applied oral medicinal agents does not allow the antibacterial agents to penetrate into the periodontal pocket where they are needed. Irrigation of the pockets with these agents has shown some effects on gingivitis, but the short time of exposure with irrigation solutions and the rapid removal of any therapeutic agent by the outward flow of the crevicular fluid make this type of treatment ineffective with severe cases of periodontitis.

The most recent proposed methods of treating periodontitis with the local delivery of chemotherapeutic agents have involved the placement of these agents directly into the periodontal pocket. These include the cellulose hollow fibers loaded with tetracycline described in U.S. Pat. No. 4,175,326 to Goodson, the ethylcellulose films loaded with metronidazole described in U.S. Pat. No. 4,568,535 to Loesche, the absorbable putty-like material described in U.S. Pat. No. 4,568,536 to Kronenthal, the ethylene vinyl acetate fibers loaded with tetracycline described in the European patent application No. 84401985.1 to Goodson, and the biodegradable microspheres and matrix described in U.S. Pat. No. 4,685,883 to Jernberg. All of these delivery systems involve placing the product directly into the periodontal pocket.

Although the space between the gingival tissue and the tooth in periodontal disease is called a pocket, it is really only a potential space in which bacteria can grow. The insertion of a delivery system within this potential space is more difficult than the simple placement of a material within a well-defined pocket. Moreover, the shape of the pocket or potential space is not regular, but often contoured based upon the shape of the tooth and the extent of the disease. Thus, placement of a film or fiber within the pocket requires careful fitting to fill the pocket but not extend beyond the gingival margin. Any material extending outside the pocket will be removed by normal oral hygiene procedures unless the material is either adhered to the tissue or tooth or covered by a periodontal dressing.

In addition to the retention problems associated with normal dental care, the outward flow of crevicular fluid and the mechanical action of the teeth and the gums during eating cause most materials placed within the periodontal pocket to be expelled in a relatively short time. It is well known that carbon particles placed within a periodontal pocket are all displaced within a few hours. Because of these retention problems, most periodontal delivery systems for chemotherapeutic agents are either adhesively bound to the tooth or the tissue within the pocket. However, adhesion to a wet surface such as that within the pocket is extremely difficult and normally the adhesion deteriorates rapidly. Thus, retention within the pocket is short-lived.

The other solution to retention of a delivery system within the pocket is to use a periodontal dressing to cover the pocket. Periodontal dressings are also adhesives and their adhesion to wet surfaces such as a tooth or gum tissue is difficult; and most periodontal dressings do not adhere long within the mouth. In addition, they are uncomfortable to the wearer and they tend to collect food particles and bacteria.

Because of these problems with proper placement of a local delivery system within the periodontal pocket and the retention of the system for sufficient time to kill all of the periodontal pathogens, there is a need for a better delivery system to deliver chemotherapeutic agents to the site of infection. Moreover, recent research indicates that the bacteria often responsible for periodontal disease exist not only in the periodontal pocket but also within the gingival tissue. This is especially true for localized juvenile periodontitis. The only way to treat this form of periodontal disease has been to administer systemic antibiotics which can attack the bacterial infection within the gingival tissue itself. Several researchers have recently shown that the bacteria responsible for periodontal disease have also been found in the tissue of patients with normal adult periodontitis.

Thus, delivery systems containing chemotherapeutic agents when placed within the periodontal pocket will kill the bacteria there, but these agents will not penetrate the gingival tissue to destroy the bacteria located intragingivally. These bacteria subsequently repopulate the periodontal pocket after the chemotherapeutic agent has been totally released or exhausted. There is therefore a need for a local delivery system that will destroy not only the periodontal pathogens within the periodontal pocket but also within the gingival tissues.

SUMMARY OF THE PRESENT INVENTION

The present invention relates to the use of controlled release systems for the delivery of chemotherapeutic agents to localized sites in the mouth for the treatment of periodontal disease. The method of treatment involves the placement of a polymeric delivery system directly into the gingival tissue that is infected rather than into the periodontal pocket that is formed between the infected tissue and the tooth.

The polymeric delivery system may consist of microspheres, microcapsules, nanoparticles, liposomes, fibers, rods, films, or spheres. They may be fabricated from either biodegradable or nonbiodegradable polymers although delivery systems fabricated from biodegradable polymers are preferred because they do not require removal after the chemotherapeutic agent has been released. Also preferred are the delivery systems in the form of microspheres, microcapsules, nanoparticles, and liposomes which can be injected directly into the gingival tissue. Liquid polymeric systems that can be injected into the gingival tissue to form solid implants are also preferred delivery systems.

When injected into the gingival tissue, the polymeric delivery systems release the bioactive agent directly into the infected tissue. The bioactive agent is released by diffusion or dissolution from the polymer or if the polymer is bioerodible the agent can be released as the polymeric device erodes or biodegrades. The release of the agent creates a high concentration of active material within the gingival tissue. If the agent released is an antimicrobial, the local concentration is sufficient to destroy the bacteria causing the infection. If the agent is an anti-inflammatory drug, the concentration is sufficient to reduce the inflammation within the tissue. Because the gingival crevicular fluid in the periodontal pocket is formed from serum from within the gingival tissue, the active agent is transported to the periodontal pocket as the serum flows out of the tissue. If the active agent is an antimicrobial, the intragingival delivery system can achieve concentrations of drug sufficient to kill the bacteria both within the tissue as well as in the periodontal pocket.

This system provides a significant advantage over delivery systems placed within the periodontal pocket where the outward flow of crevicular fluid tends to remove the active agent from the pocket as it is released. This loss of active agent has been alleviated to some extent by the placement of periodontal dressings over the opening of the pocket or the use of adhesives or sutures to close the pocket. Because of the outward flow of the crevicular fluid and the poor penetration of most active agents into tissue, the drugs released into the periodontal pocket from a delivery system placed within the pocket or outside the pocket are unable to achieve an effective concentration of drug within the infected gingival tissue.

In addition to achieving effective concentrations of the active agent within the gingival tissue and the periodontal pocket, the intragingival delivery system described in the present invention provides a reliable method for retention of the delivery system at the site of infection. The delivery system is retained by the gingival tissue until it is surgically removed or the polymer has degraded. Being located within the tissue, the intragingival delivery system (unlike a periodontal pocket delivery system) is not subject to untimely removal by the gingival crevicular fluid or the normal dental hygiene procedures such as brushing, flossing, or rinsing. Also, the location of the delivery system within the gingival tissue does not interfere with the reattachment of tissue to the tooth once the bacteria have been destroyed or the inflammation has been eliminated. A periodontal pocket delivery system prevents tissue reattachment unless it is removed or unless the delivery system degrades in a short time. An added advantage of the intragingival delivery system of this invention is that its retention and non-interference properties allow the active agent to be delivered for much longer times than those possible with a periodontal-pocket-delivery system. Thus, instead of the normal 5–14 days of delivery with a periodontal-pocket-delivery system, times of 1–6 months for delivery of bioactive agent can be achieved. This extended delivery time can be used to prevent reinfection of the site.

DETAILED DESCRIPTION OF THE INVENTION

The present invention relates to a method for treating periodontal disease by the use of an intragingival polymeric controlled delivery system. The polymeric delivery system in the form of microspheres, microcapsules, nanoparticles, or liposomes are injected directly into the infected gingival tissue where they release an active agent such as an antimicrobic or antibiotic to destroy bacteria or an anti-inflammatory agent to eliminate inflammation. The preferred delivery system consists of a biodegradable polymer such that the delivery system does not require removal once the drug has been depleted. The polymeric delivery system can also be in the form of a fiber, film, or rod which is surgically placed within the gingival tissue, but the preferred systems are those which can be injected into the tissue. A liquid polymeric system that forms a solid implant after injection into the tissue is preferred.

Although nonbiodegradable polymers can be used in this application, the biodegradable polymers are preferred because they do not require removal after drug depletion. Examples of biodegradable polymers which can be used in this application are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), methylcellulose, chitin, chitosan, collagen, and copolymers, terpolymers, or combinations or mixtures of the above materials. It is understood by those skilled in the art that the degradation times of the polymers can be adjusted by their composition, their molecular weights, catalysts, and the surface areas of the polymers.

The term drug or bioactive agent as used herein includes, without limitation, physiologically or pharmacologically active substances that act locally or systemically in the body. Representative drugs and biologically active agents to be used in this application include antimicrobials, antibiotics, anti-inflammatory agents, anti-infectives, peptide drugs, protein drugs, bone and tissue growth factors, analgesics, antigens, biological response modifiers, and the benzophenanthridine alkaloids. To those skilled in the art, other drugs or bioactive agents that can be released in an aqueous environment can be utilized in the described intragingival delivery system. Also, various forms of the drugs or bioactive agents may be used. These include, without limitation, forms such as uncharged molecules, molecular complexes, salts, ethers, esters, amides, etc., which are biologically activated when injected into the body.

The amount of drug or bioactive agent incorporated into the intragingival delivery system depends upon the desired release profile, the concentration of drug required for a biological effect, and the length of time that the drug has to be released for treatment. There is no critical upper limit on the amount of drug incorporated into the delivery system except for the local tissue irritation or the toxicity of the drug. The lower limit of drug incorporated into the delivery system is dependent simply upon the activity of the drug and the length of time needed for treatment.

With certain drugs and polymers, the drug will be released by diffusion from the polymer matrix. The rate of release will be described by Fick's Law of Diffusion for polymeric systems. If the matrix is a monolithic device, the release rate will be first-order in which there is a burst of drug initially followed by a gradually declining rate. If a reservoir device is used, the release rate will be zero-order in which there is a constant rate of release until the drug has been depleted. For other drugs and polymer, the drug will be released by simple dissolution in which the loading of drug and the porosity of the polymeric delivery system will control the rate of delivery. For other drugs, the release will depend upon the degradation rate of the polymer. The molecular weight of these drugs are so high that they will not diffuse through the matrix polymer and the only way for them to be released is for the polymer to erode or fragment due to biodegradation.

The drug and the polymer can be blended together using a variety of methods. The intimacy of mixing, particle size, and particle shape can be varied according to the intended use. High homogeneity can be obtained by mixing the components in the molten state, cooling, and grinding the resulting solid. The same type of homogeneity can be achieved if both components are dissolved in a common solvent, the solvent removed to give a film, and the film ground into a powder. These particles can be sieved to obtain the desired particle size for injection and for drug release. These particles as prepared constitute a monolithic delivery system in which the drug is distributed within the polymer matrix. As such the rate of release will be first order.

However, the particles can be converted to reservoir systems by coating them with a layer of polymer which serves as a rate-controlling membrane. The particles can be coated by several methods including spray drying, fluid-bed coating, or microencapsulation. Although microencapsulation can be used to coat drug/polymer particles already formed, it can also be used directly to form microspheres or microcapsules containing drug using a variety of methods known to those skilled in the art. These include solvent evaporation, phase separation, interfacial polymerization, hot melt, and spray drying. The type of polymer used for the coating, the uniformity of the coating, the thickness of the coating, and the size of the microspheres or microcapsules can be used to control the release of drug.

Other small particles which can be used for injection include liposomes. These drug delivery forms are formed by encapsulating various drugs in lipid bilayers. The liposomes formed are extremely small and can be injected easily into the body or the blood stream. The other particles or microcapsules are injected as fluid suspensions from syringes into subcutaneous or muscular tissue. Water or aqueous solutions of sodium chloride or sodium carboxymethyl cellulose can be used for these injections. Oils such as sesame or peanut may also be used for injection. If the polymer is soluble in a biocompatible solvent that once injected into the body disperses and leaves the polymer to form a solid, then the drug also dissolved or dispersed in the polymer solution may be injected directly into the body to form a solid implant. Also, if the polymer is injected into the body as a liquid prepolymer and then polymerizes further or crosslinks to form a solid, then the drug dispersed in the liquid prepolymer can be injected to form a solid implant.

For the other implants which are solids as formed, then a surgical incision or the use of a trochar is needed for implantation. These solid implants may be in the form of fibers, films, rods, cylinders, and pellets. The fibers can be formed by melt extrusion if the drug is stable at the melt-spinning temperature or by solution spinning where polymer is soluble in a solvent that is compatible with the drug. Rods and cylinders can be formed by the same method or they can be formed by injection molding or compression molding. Pellets can also be formed by compression molding or injection molding.

DETAILED DESCRIPTION OF EXAMPLES

The following examples are set forth as representative of the present invention. These examples are not to be construed as limiting the scope of the invention as these and other equivalent embodiments will be apparent in view of the present disclosure and accompanying claims.

EXAMPLE 1

Poly(DL-lactide) (DL-PLA) with an inherent viscosity of 0.26 dL/g and a theoretical molecular weight of approximately 10,000 daltons was prepared by the ring-opening polymerization of DL-lactide using lauryl alcohol as the initiator and stannous chloride as the catalyst. The polymer was dissolved in N-methyl-2-pyrrolidone to give a 74% by weight solution. Sanguinarine hydrochloride as an orange powder was added to the polymer solution to give a 5% by weight dispersion of the drug in the polymer solution. The dispersion when added to water or saline solution formed a deep orange-colored solid precipitate which released the active drug over a period of two weeks.

EXAMPLE 2

Ethoxydihydrosanguinarine, the ethoxy ester of sanguinarine, was added to the same DL-PLA solution as described in Example 1 to give a 5% by weight solution of the drug. The light brown solution when injected into water or a saline solution gave a slightly orange-colored solid precipitate which released the drug as sanguinarine over a period of two weeks.

EXAMPLE 3

The two formulations described in Examples 1 and 2 were placed in 1-mL disposable syringes fitted with 21 gauge, 1.5-inch needles. Each formulation was then injected into the gingival tissue of healthy beagle dogs with artificially-created periodontal pockets. The needle was placed so that the formulation penetrated through the tissue into the periodontal pocket. As the formulation was forced from the syringe, it filled up the pocket with a rapidly solidifying mass. The needle was then withdrawn from the injection site while maintaining a flow of liquid. In this manner, both the periodontal pocket and the injection site in the gingival tissue were filled with the solid implant. After several days, the material in the periodontal pocket had been completely dislodged. However, the material in the tissue injection site was still visible. There were no signs of irritation or inflammation at the injection sites.

EXAMPLE 4

Tetracycline hydrochloride was added to the same DL-PLA solution as described in Example 1 to give a 5% by weight dispersion of drug in the solution. After standing overnight, the drug had dissolved completely into the polymer solution to give a light yellow solution. When injected into an aqueous or saline solution, the polymer coagulated to form a solid which slowly released tetracycline over a time of several weeks.

EXAMPLE 5

Poly(DL-lactide-co-glycolide) was prepared by the ring-opening polymerization of a mixture of DL-lactide and glycolide using lauryl alcohol as the initiator and stannous chloride as the catalyst. The proportions of the two monomers were adjusted so that the final copolymer (DL-PLG) had a 50:50 ratio of the two monomers as determined by nuclear magnetic resonance spectrophotometry. The initiator was also adjusted to give a copolymer with a theoretical molecular weight of 1500 daltons. The copolymer was dissolved in N-methyl-2-pyrrolidone to give a 70% by weight polymer solution. Tetracycline as the free base was added to the polymer solution to give a 2.4% by weight solution of the drug in the polymer solution. The light yellow solution when added to water or saline formed a solid matrix as the polymer coagulated. The drug was released from the polymeric matrix over a period of two weeks.

EXAMPLE 6

Tetracycline hydrochloride was added to the same DL-PLG solution as described in Example 5 to give a 2% by weight dispersion. After standing overnight, the drug dissolved completely in the polymer solution. The solid that formed when the solution was added to water or saline released the drug at a controlled rate for a time of two weeks.

EXAMPLE 7

DL-PLA with an inherent viscosity of 0.26 dL/g and a theoretical molecular weight of approximately 10,000 daltons was dissolved in methylene chloride to give a clear viscous solution. To this polymer solution was added ethoxydihydrosanguinarine which dissolved to give a light brown solution with 5% by weight of drug. The solution of polymer and drug was poured into a shallow dish and the methylene chloride evaporated to form a homogenous film. The dry film was then ground to give small particles of polymer/drug which could be suspended in an aqueous injection vehicle and injected directly into tissue using a standard syringe and needle.

EXAMPLE 8

Sanguinarine chloride was added to the same DL-PLA solution as described in Example 7 to give a 5% by weight dispersion. The dispersion was poured into a shallow dish and the methylene chloride evaporated to form a film with the particles of drug dispersed uniformly within the polymer matrix. The film was then ground to give small particles of polymer/drug which could be suspended in an aqueous injection vehicle and injected directly into tissue using a standard syringe and needle.

What is claimed is:

1. A method for treatment of periodontal disease by control delivery of a bioactive agent to a localized site within infected gingival tissue of a patient, which comprises: forming a delivery system of the bioactive agent, a liquid carrier, and a water-insoluble biodegradable polymer that forms and remains a solid when coming in contact with body fluids; and inserting the delivery system into the an internal region of the infected gingival tissue whereupon the liquid carrier disperses and a particulate or solid-body implant of the biodegradable polymer containing the bioactive agent is formed within the gingival tissue.

2. A method according to claim 1 wherein bioactive agent is selected from the group consisting of an antimicrobial agent, an antibiotic agent, an anti-inflammatory agent, an anti-infective agent, a peptide, a protein, a growth factor, an antigen, and a biological response modifier.

3. A method according to claim 1 wherein the biodegradable poller has the form of particles within the delivery system and the chemotherapeutic agent is incorporated within the particles.

4. A method according to claim 3 wherein the particulate form is microspheres, microcapsules, nanoparticles, or liposomes.

5. A method according to claim 1 wherein the biodegradable poller is dissolved or dispersed in the liquid carrier and the poller is capable of forming a solid-body implant when the system contacts body fluid.

6. A method according to claim 1 wherein the biodegradable polymer is selected from the group consisting of polylactides, polyglycolides, polycaprolactones, polyanhydrides, polyamides, polyurethanes, polyesteramides, polyothoesters, polydioxanones, polyacetals, polyketals, polycarbonates, polyphosphazenes, polyhydroxybutyrates, polyhydroxyvalerates, polyalkylene oxalates, polyalkylene succinates, poly(malic acid), poly(amino acids), collagen and copolymers and terpolymers of these materials.

7. A method in accordance with claim 1 in which said insertion is accomplished with a syringe apparatus.

8. A method in accordance with claim 1 in which the delivery system comprises a drug dissolved or dispersed in a liquid non-cross linked polymer that polymerizes or crosslinks to form a solid implant after injection into said tissue.

9. A method in accordance with claim 1 which the drug is selected from tetracycline, chlorhexidine, metronidazole, minocycline, clindamycin, sanguinarine, sanguinarine acetate, ethoxydihydrosanguinarine, sanguirubine, sanguilutine, chelirubine, chelerythrine, chelilutine, acetylsalicyclic acid, acetaminophen, ibuprofen, flurbiprofen, ketanserin, bone morphogenetic protein, fibronectin, fibrololast growth factor, platelet derived growth factor, transforming growth factor, and endothelial cell growth factor.

10. A method in accordance with claim 1, wherein said agent is selected from the group consisting of sanguinarine hydrochloride, ethoxydihydrosanguinarine, sanguinarine acetate, chlorhexidine diacetate, chlorhexidine gluconate, tetracycline, and tetracycline hydrochloride; and wherein said polymer is selected from the group consisting of poly(DL-lactide) and poly(DL-lactide-co-glycolide).

11. A method in accordance with claim 1, wherein said agent is present in said polymer at a concentration in the range of about 1 to 80% by weight.

12. A method in accordance with claim 1, wherein said agent is present in said polymer at a concentration in the range of about 10 to 40% by weight.

13. A method in accordance with claim 10, wherein said agent and said polymer are present in a liquid carrier.

14. A method in accordance with claim 13, wherein said liquid carrier polymer are present in a liquid carrier. comprises a solvent for said agent and said polymer.

15. A method in accordance with claim 1 wherein the delivery system is inserted by injection or implantation.

* * * * *

UNITED STATES PATENT AND TRADEMARK OFFICE
CERTIFICATE OF CORRECTION

PATENT NO. : 5,324,520
DATED : June 28, 1994
INVENTOR(S) : DUNN ET AL

It is certified that error appears in the above-indentified patent and that said Letters Patent is hereby corrected as shown below:

On the title page: Item

At [75], line 3, please delete "Louisville" and insert therefor --Westminster--.

Column 8, line 14, please delete in the first instance "the"; line 19, after "wherein", please insert --the--; line 27, please delete "chemotherapeutic" and insert therefor --bioactive--; and line 53, after "claim 1", please insert --in--.

Signed and Sealed this

Eighth Day of August, 1995

Attest:

BRUCE LEHMAN

Attesting Officer

Commissioner of Patents and Trademarks